United States Patent [19]
Chiaramonte et al.

[11] 4,445,862
[45] May 1, 1984

[54] PRECISION PONTIC AND METHOD FOR MAKING IT

[75] Inventors: Vincent Chiaramonte; Alice Barkow, both of Lindenhurst, N.Y.

[73] Assignee: Mont-Cler Appliances Inc., Lindenhurst, N.Y.

[21] Appl. No.: 324,865

[22] Filed: Nov. 25, 1981

[51] Int. Cl.³ .............................................. A61C 13/10
[52] U.S. Cl. .................................................... 433/191
[58] Field of Search ................ 433/181, 183, 191, 213

[56] References Cited
U.S. PATENT DOCUMENTS
251,460 12/1881 Register .............................. 433/191

Primary Examiner—Robert Peshock
Attorney, Agent, or Firm—James P. Malone

[57] ABSTRACT

Process of making a post for inserting a false tooth in a vacant space between first and second good teeth having the following steps. Cut first and second small indentations in the sides of each first and second good tooth facing the vacant space. Make a plaster model of the first and second good teeth. Insert wax in the gum saddle between the two existing teeth of the model. Insert pontic having interior and exterior portions, one portion having a first wing and the other portion having a second wing. Apply wax to the first wing so that it extends into the first indentation. Apply wax to the second wing so that it extends into the second indentation. Remove the pontic portions separately with the wax attached to them with the saddle wax adhering to the lingual pontic portion. Cast each pontic portion separately by the lost wax process. Whereby the two castings may be inserted separately in the first and second indentations and fastened together.

6 Claims, 24 Drawing Figures

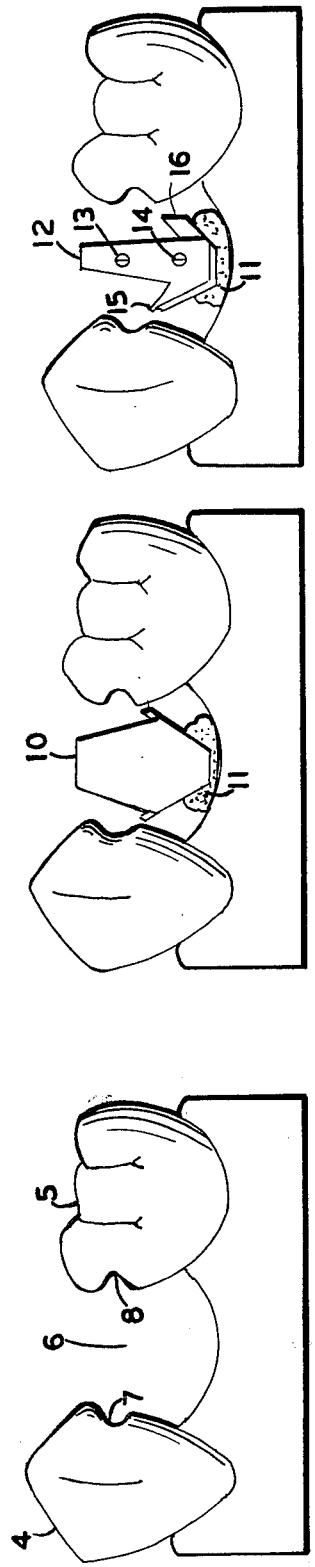
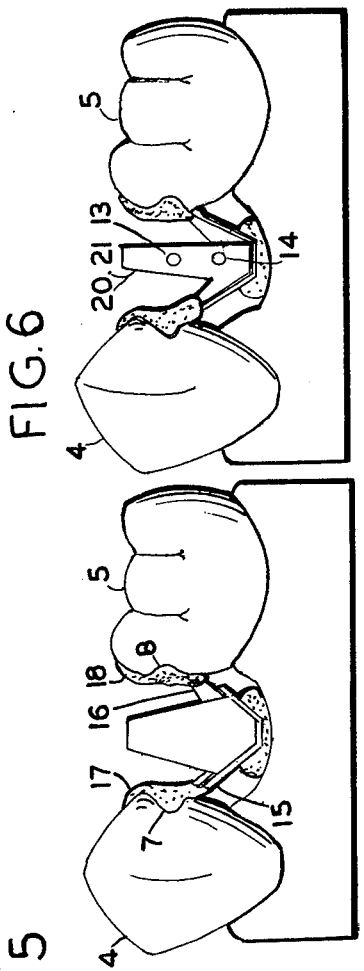
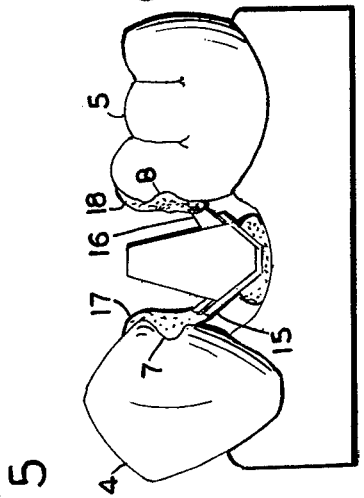
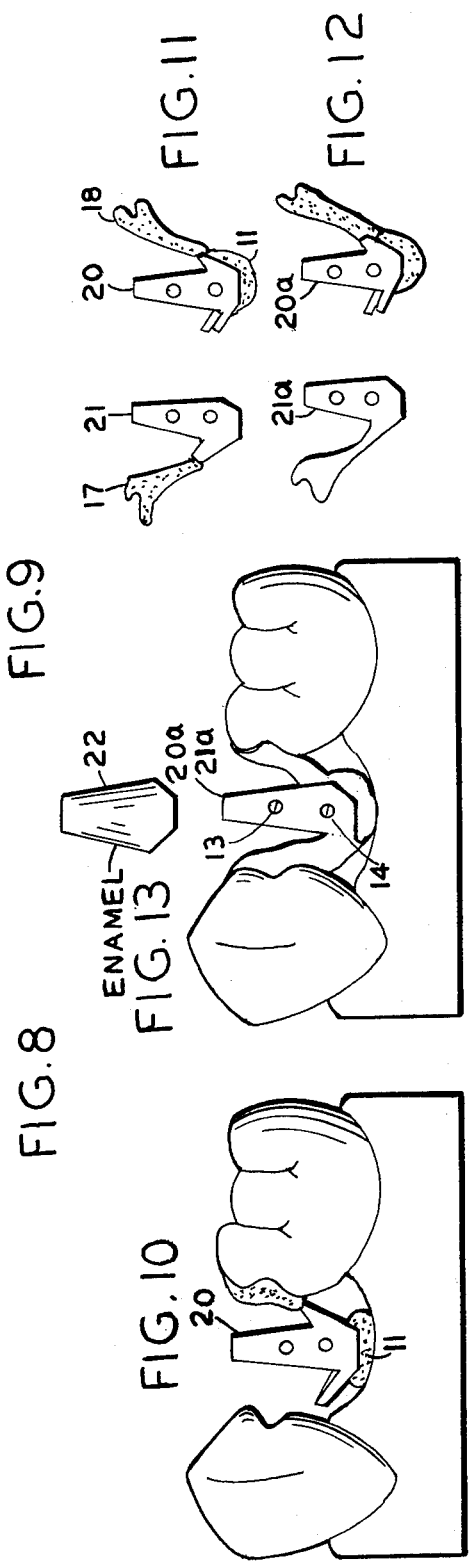

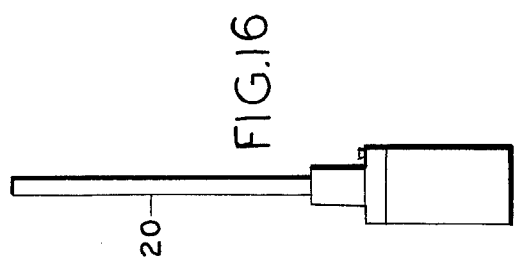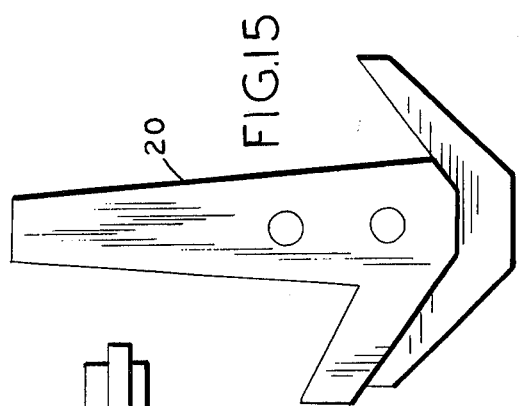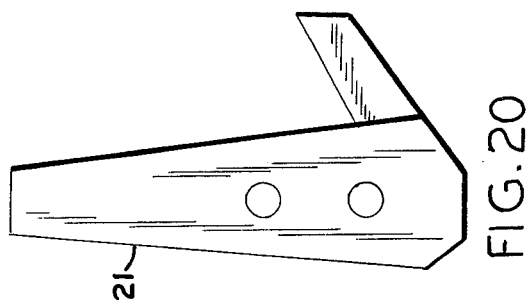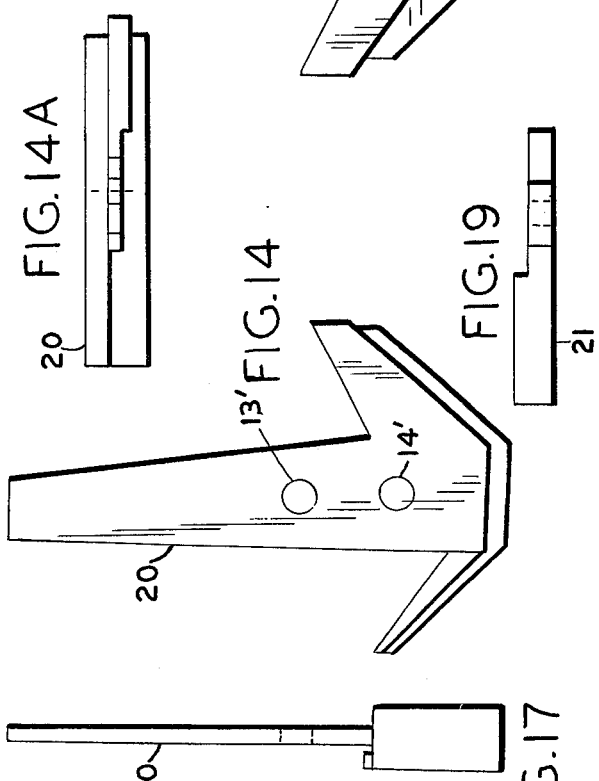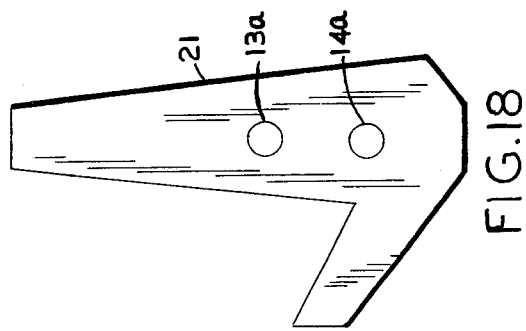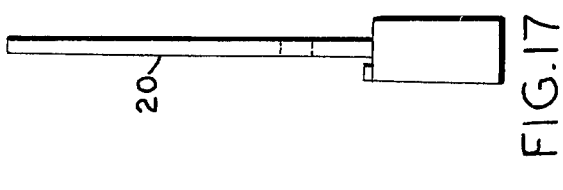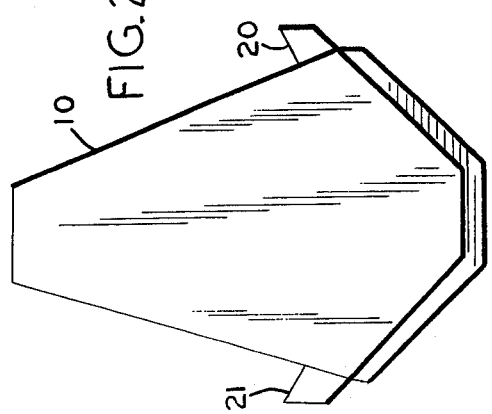

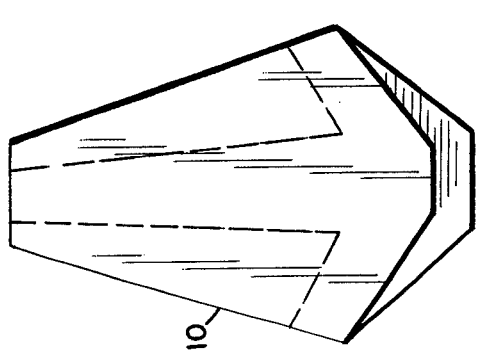
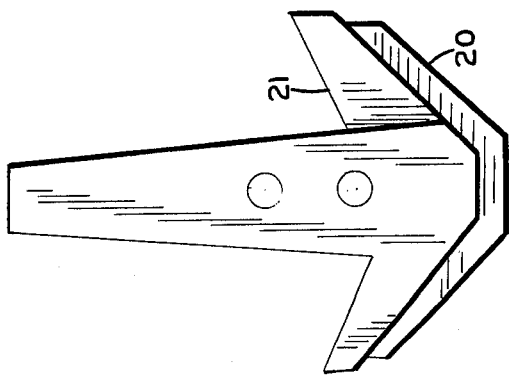
FIG. 23
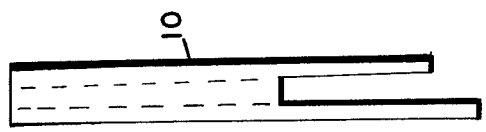
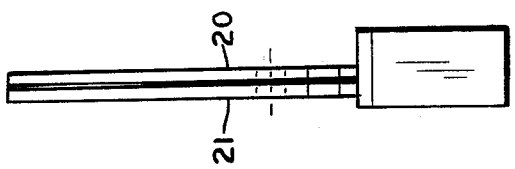
FIG. 22
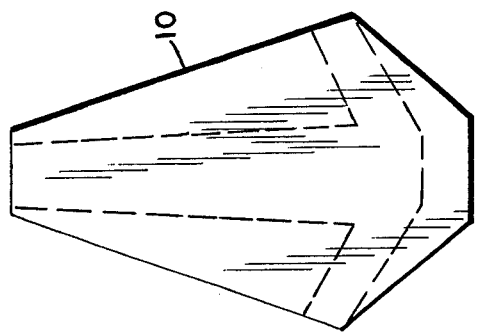
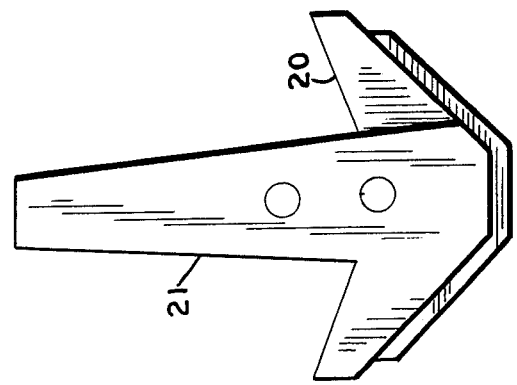
FIG. 21

PRECISION PONTIC AND METHOD FOR MAKING IT

TECHNICAL FIELD

This invention relates to tooth restoration and more particular to a precision pontic and the method for making it.

PRIOR ART PROCEDURE

Patient visits Dentist to have missing tooth replaced.

Dentist administers anesthetic to patient. Either needle or gas.

Dentist cuts down two adjacent healthy teeth to a cone shape called a preparation.

Dentist takes an extremely involved impression of the area of the prepared teeth which is expensive and difficult.

The impression is then sent to the Laboratory for the frame to be constructed.

The Laboratory then sends the Dentist the fabricated frame to try on the patient.

The Dentist sends the frame back to the Laboratory for completion if all went well.

The Laboratory then completes the case with the veneering enamel on all three teeth. Approximately double the cost to the Dentist compared to this invention.

The Dentist then cements it in the patient's mouth after additional anesthetic.

THE PRESENT INVENTION

The present invention provides new method for placing a false tooth in the mouth permanently. The method of the present invention eliminates the need for anesthesia and requires less Dentist time, less Laboratory time and less cost than the prior methods.

OBJECTS OF THE INVENTION

The principal object of the invention is to provide a new and improved method of permanently placing a tooth in the mouth.

Another object of the invention is to provide a new and improved method of placing a tooth in the mouth which takes less time by the Dentist and by the Laboratory and therefore is less costly than the prior methods.

Another object of the invention is to replace a missing tooth in the mouth, permanently, without involving the "pulp" of the adjacent teeth.

Another object of the invention is to have the adjacent teeth not "cut down" to replace the missing tooth.

Another object of the invention is to eleiminate the need for anesthetic for the patient.

Another object of the invention is to allow the Dentist to spend less time with the patient allowing him to attend to more patients.

Another object of the invention is to eliminate the use of "temporary crowns" giving more comfort to the patient.

Another object of the invention is to simplify the Laboratory procedure.

Another object of the invention is much less cost to the patient.

Another object of the invention is much more convenience for all involved.

Another object of the invention is to eliminate the need for cementing. However, with this invention, cement will provide an insurance against bacteria seepage.

Another object of the invention is to provide a new and improved process of mounting the post for inserting a false tooth in a vacant space.

Another object of the invention is to provide new and improved apparatus for mounting a post for inserting a single false tooth in a vacant space between two good teeth having first and second small indentations in the sides of each good tooth facing the vacant space, comprising: a pontic having interior and exterior portions, one portion having a first wing and the other portion having a second wing.

These and other objects of the invention will be apparent from the following specification and drawings of which:

FIGS. 5 to 13 are diagrams illustrating the method of the present invention.

FIGS. 14 to 24 are enlarged detail drawings showing the construction of the plastic pontic members and coping.

FIGS. 1 to 4 show the prior art procedure.

Patient visits Dentist to have missing tooth 3 replaced.

Dentist administers anesthetic to patient. Either needle or gas.

Dentist cuts down two adjacent healthy teeth, 1 and 2, each to a cone shape, 1', 2', called a preparation.

Dentist takes an extremely involved impression of the area of the prepared teeth which is expensive and difficult.

The impression is then sent to the Laboratory for the frame to be constructed.

The Laboratory then sends the Dentist the fabricated frame 3a, to try on the patient.

The Dentist sends the frame back to the Laboratory for completion if all went well.

The Laboratory then completes the case with the veneering enamel 1a, 2a, 3a, on all three teeth. This is approximately double the cost to the Dentist compared to this invention.

The Dentist then cements it in the patient'mouth after additional anesthetic.

The procedure of the present invention is as follows:

Patient vists Dentist.

A simple series of non-parallel grooves are cut into the adjacent teeth just into the enamel and not the 'pulp' of the tooth no pain to the patient and no anesthetic.

Simple 'algenate' impressions are taken and poured immediately.

Impressions are sent to the Laboratory.

Laboratory sends back completed bridge to Dentist.

Dentist places and locks bridge in patient's mouth with screws in the bridge. Cement in the groove will protect and seal off the tooth from possible decay, it is not used actually to cement the bridge in place. The bridge is retained by the relationship of non-parallel grooves in the adjacent teeth after the invention is locked in place with the screws. The only way the bridge can be removed is by unscrewing the screws and removing each section independently.

FIGS. 1 to 4 show the prior art method.

Figure 1:
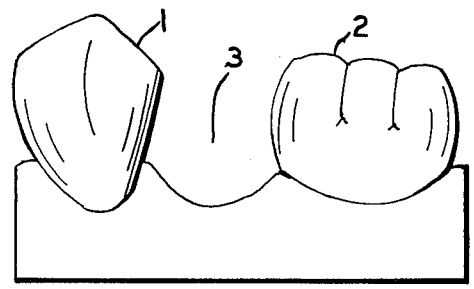
FIGS. 1 to 4 are diagrams illustrating the prior art method.

FIG. 1 shows two good teeth, 1 and 2 on the sides of the cavity 3.

Figure 2:
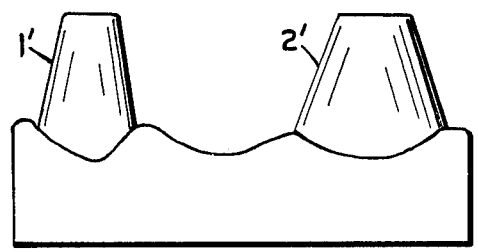

FIG. 2 shows the two good teeth ground down to a truncated cone shape 1', 2'.

Figure 3:
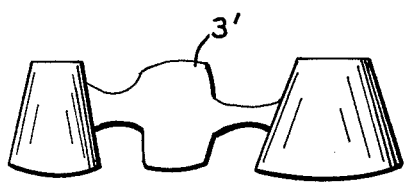

FIG. 3 shows a metal frame 3' adapted to fit over the teeth shown in FIG. 2.

Figure 4:
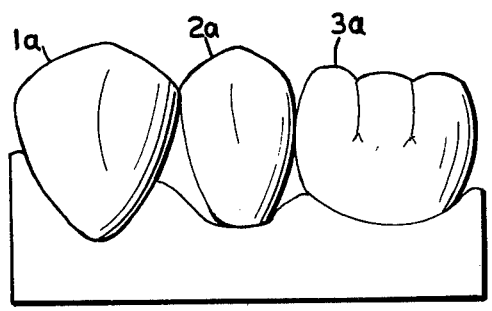

FIG. 4 shows the frame with enamel coating forming the teeth 1a, 2a and 3a.

FIGS. 5 to 12 illustrate the method of the present invention.

FIG. 5 shows plaster model of the good existing teeth 4 and 5 on the side of the space 6. Grooves 7 and 8 are cut in the teeth 4 and 5. The grooves are only in the enamel portion.

FIG. 6 shows the plastic pontic with coping 10, which is inserted into the space on the top of a saddle of wax 11.

FIG. 7 shows the pontic 12 with the coping removed having screws 13 and 14 and wings 15 and 16.

FIG. 8 shows wax preparation 17 mounted on the wing 15 and extending into the groove 7 of the tooth 4. Wax preparation 18 is mounted on the wing 16 and extends into the groove 8 of the tooth 5.

FIG. 9 is the same as FIG. 8 with the coping 10 removed, showing the screws 13 and 14. The screws are removed and the outer or buccal pontic portion is removed leaving the inner or lingual pontic portion 20, FIG. 10, with the saddle wax 11 attached. This portion is then also removed. The castings of each portion are made by the lost wax method.

FIG. 11 shows the inner lingual pontic 20 and the outer buccal pontic 21.

FIG. 12 shows the corresponding castings 20a, 21a. These castings are then inserted in the mouth and connected with two screws. Thereafter, the enamel veneer is applied to the post formed by the two castings 20a, 21a.

FIG. 13 shows the two cast pieces 20a, 21a inserted in the vacant space and screwed together by the screws 13 and 14. The coping is then covered with enamel veneer 22 in conventional manner and then cemented on to the post by the dentist in the final step.

FIG. 14 is a front view of the lingual section 20 of the pontic having screw holes 13', 14'.

FIG. 14A is a top view of FIG. 14.

FIG. 15 is a rear view of FIG. 14.

FIG. 16 is a side view from the left wing side of FIG. 14.

FIG. 17 is a side view from the right wing side of FIG. 1.

FIG. 18 is a front view of the buccal section 21 showing the screw holes 13a, 14a.

FIG. 19 is a top view of FIG. 18.

FIG. 20 is a rear view of FIG. 18.

FIG. 21 is an exploded view showing the assembled sections 20 and 21 and the coping 10.

FIG. 22 is a side view from the left wing side of FIG. 21.

FIG. 23 is a rear view of FIG. 21.

FIG. 24 is a front view of the assembly with the coping 10 attached. Once the pontic has been planted in the saddle wax as shown in FIG. 6, then the coping is removed by lifting it upwardly.

Laboratory Procedure:

1. Working plaster model is made of patients teeth, FIG. 5.

2. Proper size pontic is selected and luted to model FIG. 6, with wax 11.

3. Coping 10 is removed and pontic adjusted to fit in space, FIG. 7, then coping is replaced. Screws are in place and not moved. Coping has also been adjusted.

4. Wax 17, 18, is added to grooves in teeth, FIG. 8, then coping is removed, FIG. 9.

5. When wax has hardened and coping is removed, FIG. 9, the screws are carefully removed.

6. After screws are removed, the buccal section is removed carefully, FIG. 10, exposing the lingual section.

7. Both sections after removal from model, are set with copper screws in all holes 13a, 14a, etc., and sprued and invested for casting by lost wax technique.

8. The plastic pontic, FIG. 11, will completely evaporate along with the wax leaving a void in the chamber and a casting is made. Incorporated in the casting, are the copper screws, the casting is placed in the nitric acid and the screws dissolve leaving the exposed threads.

9. The castings 20a, 21a, are finished, polished, FIG. 12 and placed back on the model with the screws in place, FIG. 13.

10. The enamel veneer is applied on coping, FIG. 13 and sent to the Dentist for insertion. After the Dentist locks the castings in the mouth and is satisfied with the fit, he cements the copying and veneer in place over pontic.

The process of the present invention may also be used to replace two or more teeth.

Alternatively, in the manufacture of the plastic lingual section of the pontic, the nuts can be impregnated in the plastic.

During the casting process, the plastic evaporates and leaves the nuts clear. The casting metal casts to the nuts making them part of the final castings.

It is claimed:

1. Process of making a post for inserting a false tooth in a vacant space between first and second good teeth comprising the following steps:

cut first and second small indentations in the sides of each first and second good tooth facing the vacant space, make a plaster model of the first and second good teeth, insert wax in the gum saddle between the two existing teeth of the model, insert pontic having interior and exterior portions, one portion having a first wing and the other portion having a second wing, apply wax to the first wing so that it extends into the first indentation, apply wax to the second wing so that it extends into the second indentation, remove the pontic portions separately with the wax attached to them with the saddle wax adhering to one pontic portion, cast each pontic portion separately by the lost wax process, whereby the two castings may be inserted separately in the first and second indentations and fastened together.

2. Process as in claim 1 wherein the pontic portions are made of plastic, each pontic portion having two screw holes, one portion screw hole having threads, the one portion being cast with molded threads, whereby after the first and second castings are inserted in the first and second indentations, the two castings may be screwed together to provide a permanent post.

3. Process as in claim 1 including the following steps:
cast each pontic portion separately with a dissolvable metal screw mounted in the screw holes by the lost wax method, thereby producing castings with the screws in them,
dissolve the screws out with acid.

4. Apparatus for making a bridge post for inserting a single false tooth in a vacant space between two good teeth having first and second small indentations in the sides of each good tooth facing the vacant space, comprising:

a bridge post having interior and exterior parts, one part having a first wing and the other part having a second wing, each bridge post part having a screw hole, the screw hole in one part having threads, the wings being shaped to fit into the indentations whereby the bridge parts may be separately inserted before being fastened together in overlapping relationship to form a post.

5. Apparatus as in claim 4 wherein the pontic portions are made of plastic, each pontic part having a screw hole, the screw hole in one part having threads.

6. Apparatus as in claim 4 having enamel veneer applied to the post.

* * * * *